United States Patent [19]

Sugai et al.

[11] 4,326,846
[45] * Apr. 27, 1982

[54] DENTAL HANDPIECE

[75] Inventors: Hiroshi Sugai; Shoji Nakayama, both of Kyoto, Japan

[73] Assignee: Kabushiki Kaisha Morita Seisakusho, Kyoto, Japan

[*] Notice: The portion of the term of this patent subsequent to Jun. 24, 1997, has been disclaimed.

[21] Appl. No.: 124,451

[22] Filed: Feb. 25, 1980

Related U.S. Application Data

[63] Continuation-in-part of Ser. No. 889,646, Mar. 24, 1978.

[30] Foreign Application Priority Data

Apr. 10, 1977 [JP] Japan .................................. 52/37810

[51] Int. Cl.³ .............................................. A61C 1/12
[52] U.S. Cl. .................................................... 433/132
[58] Field of Search ................................ 433/132, 503

[56] References Cited

U.S. PATENT DOCUMENTS

| 3,055,112 | 9/1962 | Borden | 433/132 |
| 3,218,028 | 11/1965 | Borden | 433/132 |
| 3,268,205 | 8/1966 | Allen et al. | 433/132 |
| 3,298,103 | 1/1967 | Maurer | 433/132 |
| 3,324,553 | 6/1967 | Borden | 433/132 |
| 3,946,490 | 3/1976 | Sotman et al. | 433/132 |
| 3,962,789 | 6/1976 | Flatland | 433/132 |
| 4,209,293 | 6/1980 | Sugai et al. | 433/132 |

Primary Examiner—Gene Mancene
Assistant Examiner—Michael J. Foycik
Attorney, Agent, or Firm—Koda and Androlia

[57] ABSTRACT

This invention relates to a dental handpiece including turbine blades to be driven by a high-speed fluid under pressure to a turbine rotor chucking a cutting shaft, and blades are provided with openings or cutout portions located at both outside ends in a thrust direction of the blades so as to provide flange portions between the openings and the end portions of the blades and the peripheral width of the blades is larger than that of the high-speed fluid supply aperture.

3 Claims, 7 Drawing Figures

DENTAL HANDPIECE

CROSS REFERENCE TO RELATED APPLICATION

This is a continuation-in-part application of prior application Ser. No. 889,646 filed Mar. 24, 1978.

BACKGROUND OF THE INVENTION

1. Field of the Invention

This invention relates to a dental handpiece and more particularly to a dental handpiece in which an increase in the cutting torque of the handpiece is made possible by applying a simple modification to turbine blades. The range of application of this invention includes a type wherein the turbine rotor is journaled by air bearings in a thrust gap and a radial gap and a type wherein the turbine rotor is mechanically journaled by ball bearings.

2. Description of the Prior Art

When a load contrary to the direction of rotation of a tool shaft of a handpiece is applied to the tool shaft (typically, when tooth cutting is carried out), a handpiece of the type wherein the rotor is rotated at high speed is caused to stop rotation of the tool shaft at a relatively low load to thereby make cutting impossible. This fact will now be described by way of two examples below.

(1) When an inverse load is progressively applied to an air-driven turbine operated air bearing journaled type handpiece which is being rotated at a speed of 500,000 rpm, the handpiece is reduced in the number of rotations in proportion as the load is increased as shown in curve a in FIG. 6; and when it is subjected to a load of 100 g, the handpiece stops rotation and it is impossible to cut.

(2) On the other hand, although not shown, an air-driven mechanical (ball bearing) journal mechanism directed mainly toward medium-speed cutting (300,000–400,000 rpm), smaller in the number of rotations, stops in the range of 350,000–300,000 rpm when a load of 230–250 g is applied.

In an attempt to solve those drawbacks, a number of proposals have been made. U.S. Pat. No. 3,055,112 discloses a dental handpiece having an air turbine consisting of twin rows of rotor vanes on either side of a centrally disposed annular pressurized chamber. However, it does not provide blades whose width is longer than that of the fluid supplying opening, whereby the torque thus obtained is limited.

U.S. Pat. No. 25,964 (Reissue) discloses a dental handpiece whose blades have saw-like teeth thereon. As a result, some portion of the air supplied through the opening will pass through the space between the teeth causing reduction in originating torque.

U.S. Pat. No. 4,146,964 discloses a dental handpiece including a pair of oppositely facing hollow caps having turbine blades around their peripheries arranged in a staggered relationship. This dental handpiece has apertures in the middle of the blade; however, such blade is not provided with opening cuts and flanges as a single unit. Therefore, the apertures taught by U.S. Pat. No. 4,146,964 does not have much to do with the efficiency of the torque.

SUMMARY OF THE INVENTION

In view of the above facts, the present inventors, who are well aware of the importance of increasing cutting torque in high-speed and medium-speed rotations, have made various experiments and research and have realized that opening of partially communicating holes for fluid (chiefly compressed air) such as cutout portions, through holes, or slots in the turbine blades is effective for solving the problems above. Preferred embodiments of the invention will now be described by way of example only with reference to the accompanying drawings.

DETAILED DESCRIPTION OF THE INVENTION

Figure 1:
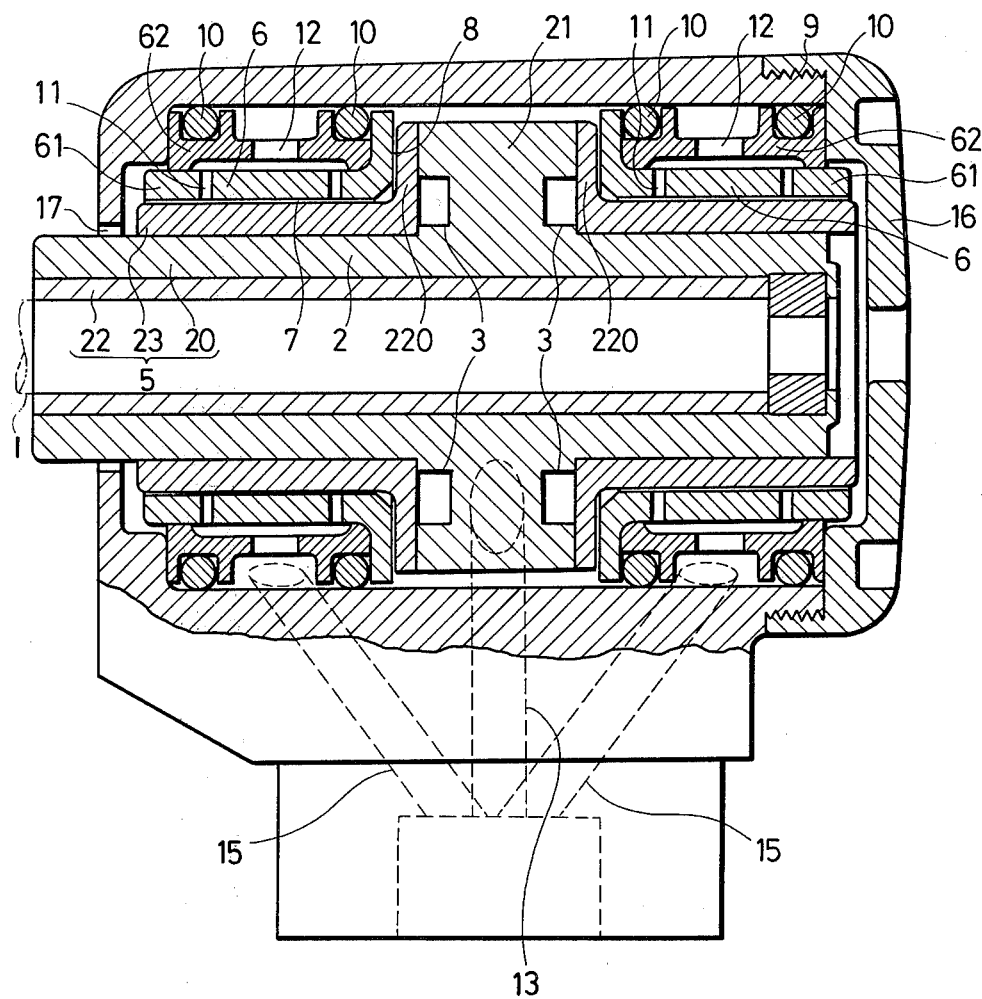
FIG. 1 is a schematic sectional view of the turbine rotor of a dental handpiece including the turbine blades according to the present invention.
Figure 2:
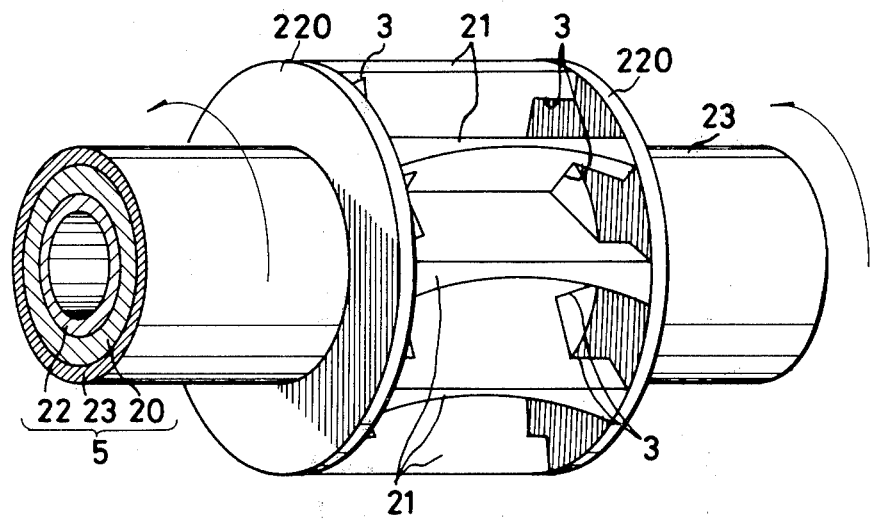
FIG. 2 is an enlarged perspective view exclusively of the turbine rotor.
Figure 3:
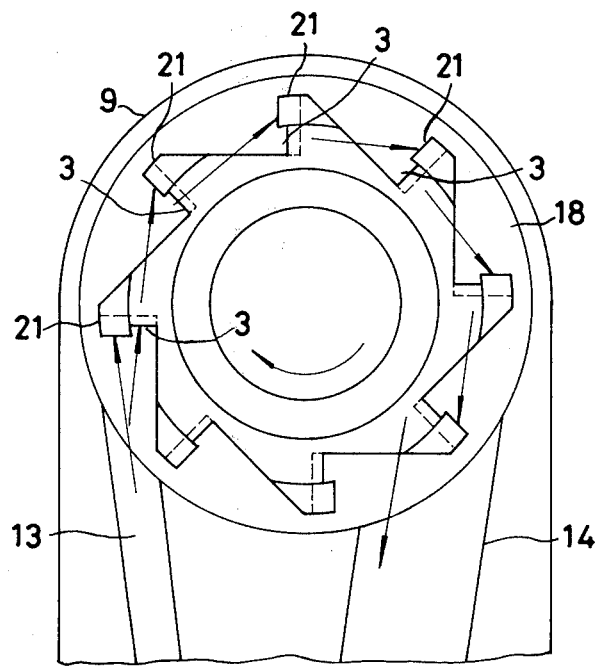
FIG. 3 is an explanatory view of an air flow passageway in the rotor of FIG. 2.
Figure 4:
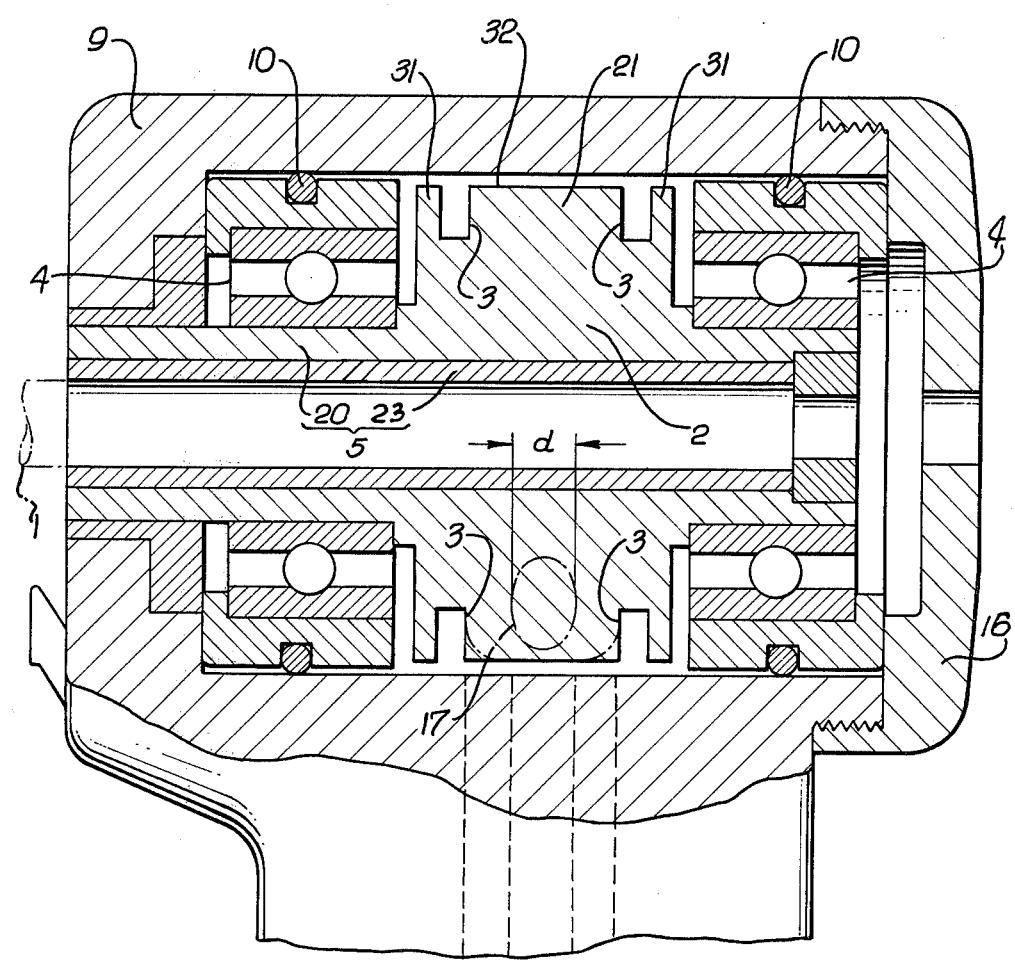
FIG. 4 is a schematic sectional view of another embodiment of the turbine rotor of the present invention.
Figure 5:
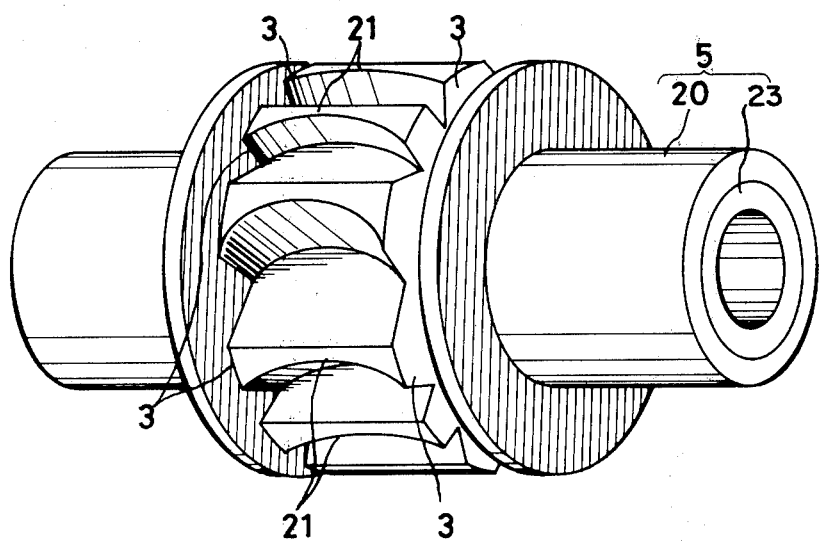
FIG. 5 is a perspective view of the rotor of FIG. 4.

According to a first embodiment of the invention illustrated in FIGS. 1 through 3, communication openings are shown in the form of cutout portions located inside both blade ends in the thrust direction of a turbine blade 21, and in a second embodiment of FIGS. 4 and 5 the openings are shown similarly in the form of cutout portions located outside both blade ends in the thrust direction of the turbine blade 21. And the turbine rotor in the first embodiment is of the air-driven turbine operated air bearing journaled type and the turbine rotor in the second embodiment is of the air-driven turbine operated mechanical bearing journaled type. In FIGS. 1 through 3, a cutting tool shaft 1 is supported by a shaft unit 5; and more particularly, the shaft unit 5 comprises a shaft 20 of the turbine rotor 2 and shaft sheaths 22 and 23 fitted into and over the shaft 20 respectively. The numeral 6 designates a bearing unit and a radial gap 7 is spacedly provided between the bearing unit 6 and the shaft unit 5, while a thrust gap 8 is spacedly provided with respect to a vertical flange 220, and O-rings 10 are retained pressedly between the outer race 62 of the bearing unit 6 and casing 9. In this manner, the bearing unit 6 is fixed to the casing 9. The bearing unit 6 is provided with air supply ports 11 and 12 to feed air to the gaps 7 and 8 respectively. The numeral 13 designates an air supply passageway for supplying the turbine blades 21 with air; 14 and exhaust passageway; 15 and air supply passageway to the bearing unit 6; 16 an end lid; and 17 designates an exhaust passageway from the bearing unit 6. It is well known as an established concept of the handpiece mechanism of this type that compressed air supplied from the air supply passageways 13 and 15 according to the mechanism described above is in charge of driving the turbine blades 21 and of air journaling of the shaft in the gaps 7 and 8. Also, the numerals 4 and 4 in FIG. 4 designate the ball bearings supporting the shaft unit 5 and the air driving mechanism of the blades 21 in this embodiment is the same as that in the first embodiment.

Since the invention is of the construction described above, the compressed air supplied under pressure from the air supply passageways 13 into rotor blades chambers 18, as illustrated in FIG. 3, collides successively with blades 21 to turn the blades and part of the air passes successively through the communication openings to thereby form a continuous air passageway for the exhaust passageway 14.

Normally in this kind of turbine mechanism it is well known that a large part of the air that strikes against the turbine 21 turns toward the circumferential wall side of the casing 9 and part of momentum at that time becomes torque of the blades 21; but because in the conventional mechanism the turbine blades 21 are blind with respect to their adjacent blades within the range of impact pressure of the air, the air that is turned after the impact pressure applied strikes hard against the inner circumference of the casing 9 and the friction produced at that time spends the aforestated momentum, with the result that energy for producing the torque of the blades 21 is decreased to thereby reduce the cutting ability of the handpiece.

Figure 6:
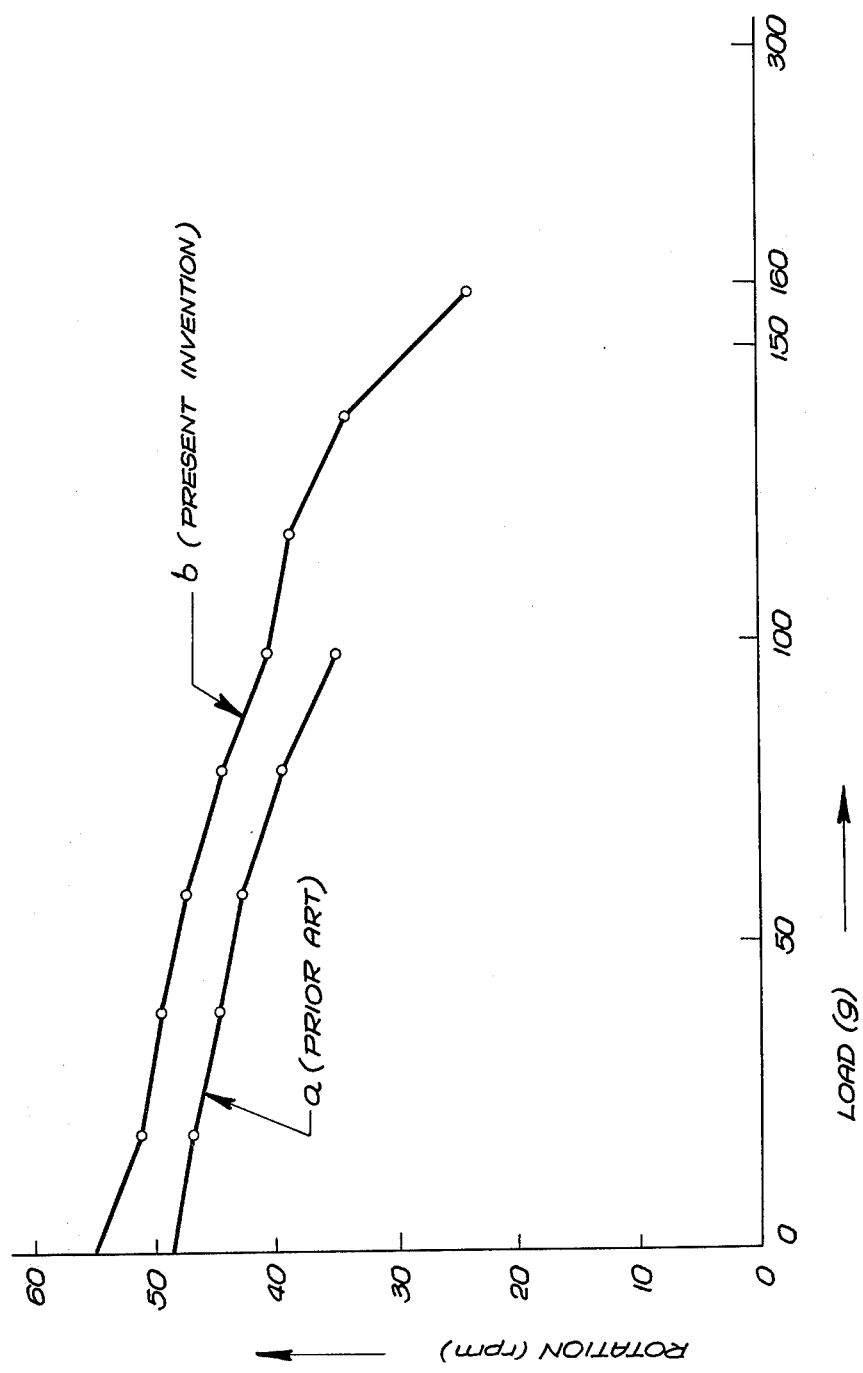
FIG. 6 is a graphic representation showing the cutting characteristics of the turbine rotors of the present invention and of the conventional type respectively.

In contrast thereto, according to the invention, the air that gave impact pressure to the turbine blade 21 comes in part through the communication opening 3 into the next turbine blade chamber 18 located in the direction of rotation and collides with the turbine blade 21 in the chamber in either of the first and second embodiments, so that the aforestated friction loss of energy due to the casing 9 is reduced and the torque of the rotor 2 is improved. To explain this fact with reference to curve b the performance curve of the present invention in FIG. 6, the curve b is always higher in the number of rotations proportionate to the addition of inverse load (in other words, higher speed of rotation and larger in torque) than curve a representative of the conventional mechanism. It further shows in FIG. 6 the rotor of the present invention can keep its cutting ability until a load up to 160 g while the prior art device can only keep its cutting ability to a load of not more than 100 g. Furthermore, as described, the curve a for the conventional mechanism becomes unable to cut under a load of 100 g and is always lower in the number of rotations than the rotor of the invention. The fact is sufficient to demonstrate a torque increase of the rotor of the present invention. Also, in the medium-speed rotation mentioned, namely in the second embodiment of the invention, the amount of load (stopping load) is 300–380 g per 450,000–350,000 rpm, while the conventional rotor turbine having no communication openings 3 in the blades thereof, as stated, stops under a load of 230–250 g per 350,000–300,000 rpm. Comparison between the two mechanisms will suffice to make it understood that the invention is increased in stopping torque in time of high-speed rotation.

Figure 7:
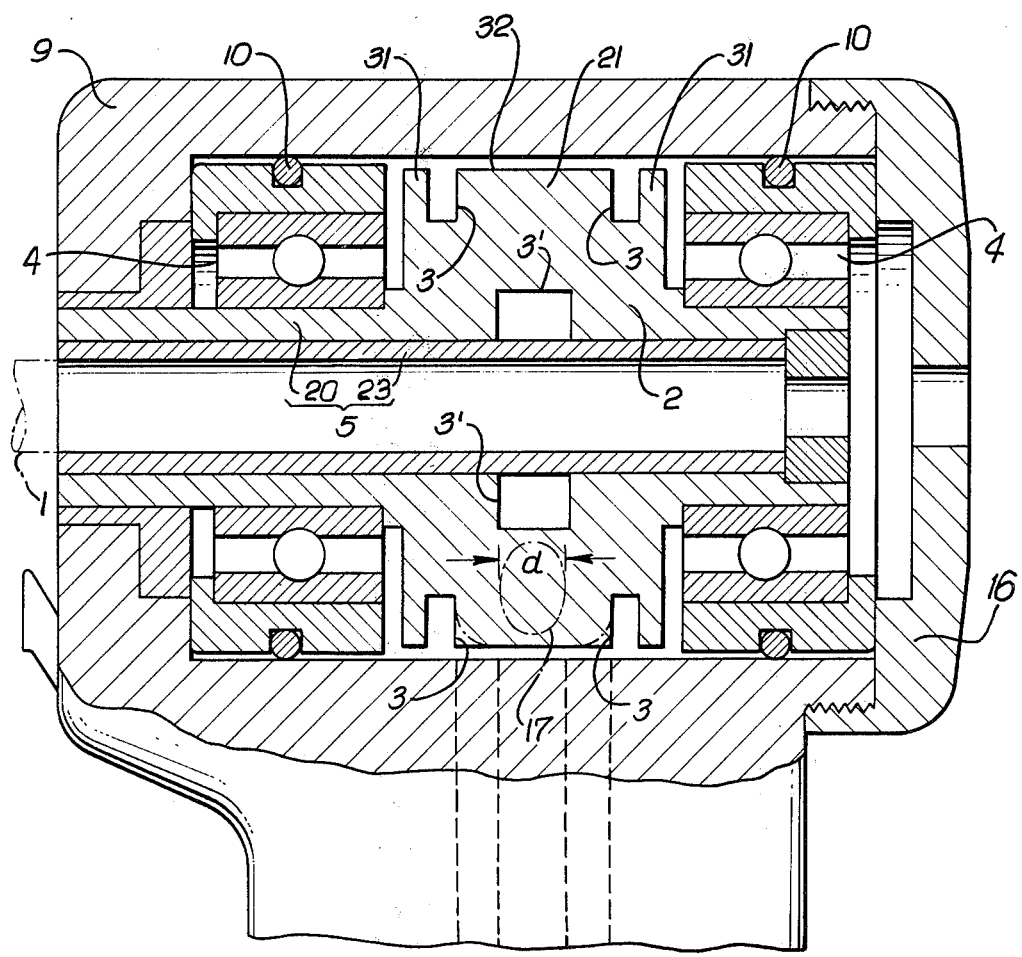
FIG. 7 is a schematic sectional view of the third embodiment of the turbine rotor of the present invention.

Shown in FIG. 7 is another embodiment of the present invention. The embodiment of FIG. 7 is substantially the same as FIG. 4 except that it includes additional gaps 3'. In addition, the embodiment FIG. 7 illustrates the flanges 31, peripheral edge 32 of the blade 21 and air-supply apperture 17. The remainder of the elements of the embodiment of FIG. 4 and a description of their interconnection and operation will be omitted.

In operation the additional gap 3' in the central portion of the blade 21 allows more exhaust gas to pass therethrough and provides an additional improvement in operation as compared to the embodiment of FIG. 4.

As hereinbefore described, the simple machining of the blades proposed by the invention is highly effective for increasing torque. It should be understood that various modifications of the invention may be made and that therefore the communication openings may be provided in the form of through holes or slots instead of the cutout openings illustrated.

We claim:

1. A dental handpiece comprising turbine blades of a single turbine driven by applying a high-speed fluid under pressure through a high-speed fluid supply aperture coupled to a turbine rotor chucking a cutting shaft, said turbine rotor being journaled in bearings and said aperture facing said blades, wherein said blades are provided with openings or cutout portion located at both outside ends in a thrust direction of said blades so as to provide flange portions between said openings and said end portions of said blades and the width of said blades at a periphery thereof is larger than that of said high-speed fluid supply aperture.

2. A dental handpiece according to claim 1, wherein said blades are further provided with circumferential openings of apertures therethrough.

3. A dental handpiece according to claim 1, wherein said high-speed fluid under pressure is compressed fluid.

* * * * *